US00PP32695P3

(12) United States Plant Patent
Grazzini

(10) Patent No.: US PP32,695 P3
(45) Date of Patent: Dec. 22, 2020

(54) *SALVIA* PLANT NAMED 'G14251'

(50) Latin Name: *Salvia farinacea*
Varietal Denomination: G14251

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 0 days.

(21) Appl. No.: 16/873,535

(22) Filed: Apr. 30, 2020

(65) Prior Publication Data

US 2020/0367418 P1 Nov. 19, 2020

(30) Foreign Application Priority Data

May 17, 2019 (CA) ..... PBR 19-9870

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Susan McCormick Ewoldt
(74) *Attorney, Agent, or Firm* — C. Anne Whealy

(57) ABSTRACT

A new and distinct cultivar of *Salvia* plant named 'G14251', characterized by its upright to outwardly spreading plant habit; vigorous growth habit and rapid growth rate; freely branching habit; dense and bushy plant form; strong and sturdy lateral branches; medium green-colored leaves; early, freely and continuous flowering habit; long and thick inflorescences with large dark violet-colored flowers; and good garden performance.

1 Drawing Sheet

Botanical designation: *Salvia farinacea.*
Cultivar denomination: 'G14251'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9870. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Salvia* plant, botanically known as *Salvia farinacea* and hereinafter referred to by the name 'G14251'.

The new *Salvia* plant is a product of a planned breeding program conducted by the Inventor in Bellefonte, Pa. The objective of the breeding program is to create new vigorous and freely-branching *Salvia* plants with attractive leaves, large flowers on long and thick inflorescences and good garden performance.

The new *Salvia* plant originated from a cross-pollination made by the Inventor on August, 2013 of a proprietary selection of *Salvia farinacea* identified as code number G2X-31942, not patented, as the female, or seed, parent with an unidentified proprietary selection of *Salvia farinacea*, not patented, as the male, or pollen, parent. The new *Salvia* plant was discovered and selected by the Inventor as a single flowering plant from within the progeny of the stated cross-pollination in a controlled greenhouse environment in Bellefonte, Pa. on Oct. 8, 2014.

Asexual reproduction of the new *Salvia* plant by vegetative terminal cuttings in Bellefonte, Pa., since October, 2014 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G14251'. These characteristics in combination distinguish 'G14251' as a new and distinct *Salvia* plant:

1. Upright to outwardly spreading plant habit.
2. Vigorous growth habit and rapid growth rate.

3. Freely branching habit; dense and bushy plant form.
4. Strong and sturdy lateral branches.
5. Medium green-colored leaves.
6. Early, freely and continuous flowering habit.
7. Long and thick inflorescences with large dark violet-colored flowers.
8. Good garden performance.

Plants of the new *Salvia* can be compared to plants of the parent selections. Plants of the new *Salvia* differ primarily from plants of the parent selections in plant and flowering habit as plants of the new *Salvia* are more uniform in plant and flowering habit than plants of the parent selections.

Plants of the new *Salvia* can be compared to plants of *Salvia farinacea* 'G13592', disclosed in U.S. Plant Pat. No. 27,860. In side-by-side comparisons, plants of the new *Salvia* differ from plants of 'G13592' in the following characteristics:

1. Leaves of plants of the new *Salvia* are darker green in color than leaves of plants of 'G13592'.
2. Plants of the new *Salvia* flower earlier and longer during the summer than plants of 'G13592'.
3. Plants of the new *Salvia* have longer inflorescences than plants of 'G13592'.
4. Plants of the new *Salvia* have larger flowers than plants of 'G13592'.

Plants of the new *Salvia* can be compared to plants of *Salvia farinacea* 'DANSALFUN1', disclosed in U.S. Plant Pat. No. 19,788. In side-by-side comparisons, plants of the new *Salvia* differ from plants of 'DANSALFUN1' in the following characteristics:

1. Plants of the new *Salvia* are larger and more vigorous than plants of 'DANSALFUN1'.
2. Leaves of plants of the new *Salvia* are darker green in color than leaves of plants of 'DANSALFUN1'.
3. Plants of the new *Salvia* flower later than plants of 'DANSALFUN1'.
4. Plants of the new *Salvia* have longer inflorescences than plants of 'DANSALFUN1'.
5. Plants of the new *Salvia* have larger flowers than plants of 'DANSALFUN1'.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

At the top of the photographic sheet (FIG. 1) is a side perspective view of a typical flowering plant of 'G14251' grown in a container and at the bottom of the photographic sheet is a close-up view of a typical flowering plant of 'G14251'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Salvia* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Salvia farinacea* 'G14251'.

Parentage:

*Female, or seed, parent.*—Proprietary selection of *Salvia farinacea* identified as code number G2X-31942, not patented.

*Male, or pollen, parent.*—Unidentified proprietary selection of *Salvia farinacea*, not patented.

Propagation:

*Type.*—Terminal vegetative cuttings.

*Time to initiate roots, summer and winter.*—About 10 to 14 days at soil temperatures about 22.2° C. and ambient temperatures about 18.3° C.

*Time to produce a rooted young plant from an unrooted cutting, summer and winter.*—About five to six weeks at soil temperatures about 22.2° C. and ambient temperatures about 18.3° C.

*Root description.*—Medium in thickness, fibrous; typically white to creamy white in color, actual color of the roots is dependent on substrate composition, water quality, fertilizer type and formulation, substrate temperature and physiological age of roots.

*Rooting habit.*—Moderately freely branching, medium density.

Plant description:

*Plant and growth habit.*—Herbaceous perennial typically grown as a container and garden plant; upright to outwardly spreading plant habit; uniform plant and flowering habit; vigorous growth habit and moderate growth rate.

*Branching habit.*—Freely basal branching with about four to five primary lateral branches each with about four secondary branches and each with four tertiary branches; bushy and dense appearance.

*Plant height.*—About 35.9 cm.

*Plant width.*—About 49.7 cm.

*Lateral branch description.*—Length: About 31 cm. Diameter: About 3.2 mm. Internode length: About 5.3 cm. Strength: Strong and sturdy. Aspect: Mostly upright to about 30° to 45° from vertical. Texture and luster: Moderately pubescent, longitudinally ridged; semi-glossy. Color, developing: Close to 144C. Color, developed: Close to 143C; along ridges, close to N187C.

Leaf description:

*Arrangement.*—Opposite, simple.

*Length.*—About 8.6 cm.

*Width.*—About 5.2 cm.

*Shape.*—Ovate.

*Apex.*—Broadly acute.

*Base.*—Cuneate.

*Margin.*—Mostly entire; proximally may be broadly crenate.

*Texture and luster, upper surface.*—Sparsely pubescent; semi-glossy.

*Texture and luster, lower surface.*—Sparsely pubescent and moderately pubescent along midrib; matte.

*Venation pattern.*—Pinnate, arcuate.

*Color.*—Developing leaves, upper surface: Close to 143A. Developing leaves, lower surface: Close to 137C. Fully expanded leaves, upper surface: Close to N137B; venation, close to 145C. Fully expanded leaves, lower surface: Close to 147B; venation, close to 145D.

*Petioles*.—Length: About 3.1 cm. Diameter: About 2 mm. Strength: Moderately strong. Texture and luster, upper and lower surfaces: Moderately to densely pubescent; matte. Color, upper surface: Close to 144B. Color, lower surface: Close to 144D.

Flower description:

*Flower arrangement and shape*.—Single bilabiate flowers arranged on erect terminal and axillary racemes; freely flowering habit with about 25 to 36 flowers developing per inflorescence and more than 450 flowers developing per plant; flowers face mostly outwardly.

*Fragrance*.—None detected.

*Natural flowering season*.—Early flowering habit, plants begin flowering about six to seven weeks after planting; plants flower from late spring until frost in Central Pennsylvania.

*Flower longevity*.—Flowers last about four to five days on the plant; flowers not persistent.

*Flower buds*.—Length: About 8 mm. Diameter: About 4 mm. Shape: Obovate. Texture and luster: Densely pubescence, velvety; matte. Color: Close to 93A, 93B and 93C.

*Inflorescence height*.—About 16.3 cm.

*Inflorescence diameter*.—About 6 cm.

*Flower diameter*.—About 1.6 cm.

*Flower length*.—About 2.3 cm.

*Flower throat diameter*.—About 5 mm.

*Flower tube length*.—About 7 mm.

*Flower tube diameter, distally*.—About 4.5 mm.

*Petals*.—Arrangement: Five petals with two upper petals fused forming a galea, two lateral petals and a single broader lower petal forming a protruding lip. Upper galea length: About 5 mm. Upper galea width: About 4 mm. Lateral petal length: About 3 mm. Lateral petal width: About 3 mm. Lower lip length: About 1.3 cm. Lower lip width: About 1.2 cm. Shape: Upper galea, hooded; lateral petals, rounded; lower lip, rounded oblong. Apex: Round. Base: Fused into a narrow tube. Margin: Entire. Texture and luster, upper surface: Pubescent; somewhat glossy. Texture and luster, lower surface: Minute pubescence; somewhat glossy. Texture and luster, throat: Smooth, glabrous; slightly glossy. Texture and luster, tube: Sparsely pubescent; moderately glossy. Color: Galea, when opening and fully opened, upper surface: Close to 93A; venation, close to 93A; color does not fade with development. Galea, when opening and fully opened, lower surface: Close to 93B to 93C; venation, close to 93B to 93C; color does not fade with development. Lateral petals, when opening and fully opened, upper surface: Close to 93B; venation, close to 93B; color does not fade with development. Lateral petals, when opening and fully opened, lower surface: Close to 93B to 93C; venation, close to 93B to 93C; color does not fade with development. Lower lip, when opening and fully opened, upper surface: Close to 93C; stripes, close to N155A; venation, close to 93C; color does not fade with development. Lower lip, when opening and fully opened, lower surface: Close to 91A; center, close to 91D; venation, close to 91A and 91D; color does not fade with development. Throat: Close to N155A; venation, close to N155A. Tube: Close to NN155C; venation, close to NN155C.

*Calyx*.—Arrangement: Five sepals fused to form a tubular bilabiate calyx. Length: About 8 mm. Diameter: About 5 mm. Sepal shape: Roughly deltoid. Sepal apex: Slightly retuse. Sepal margin: Entire. Sepal texture and luster, inner surface: Smooth, glabrous; matte. Texture and luster, outer surface: Densely pubescent; matte. Color: When developing and fully developed, inner surface: Close to 93C; distally, close to 93A. When developing and fully developed, outer surface: Close to 93C; distally, close to 93A.

*Peduncles*.—Length: About 11.5 cm. Diameter: About 3 mm. Strength: Strong. Aspect: Mostly erect. Texture and luster: Densely pubescent, longitudinally ridged; matte. Color: Close to 138B; along the ridges, close to 93D.

*Pedicels*.—Length: About 3 mm. Diameter: Less than 1 mm. Strength: Strong, flexible. Aspect: About 90° from peduncle axis. Texture and luster: Moderately pubescent; matte. Color: Close to N77C.

*Reproductive organs*.—Stamens: Quantity per flower: Two. Filament length: About 7 mm. Filament color: Close to NN155D. Anther size: About 2 mm by 1 mm. Anther shape: Oblong. Anther color: Close to 79B. Pollen amount: Scarce. Pollen color: Close to 13A. Pistils: Quantity per flower: One. Pistil length: About 1.1 cm. Stigma diameter: About 3 mm. Stigma shape: Bipartite. Stigma color: Close to 94A. Style length: About 9 mm. Style color: Close to NN155B. Ovary color: Close to 145B.

*Seeds and fruits*.—To date, seed and fruit production has not been observed on plants of the new *Salvia* plant.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind and temperatures ranging from 13° C. to 38° C.

It is claimed:

1. A new and distinct *Salvia* plant named 'G14251' as illustrated and described.

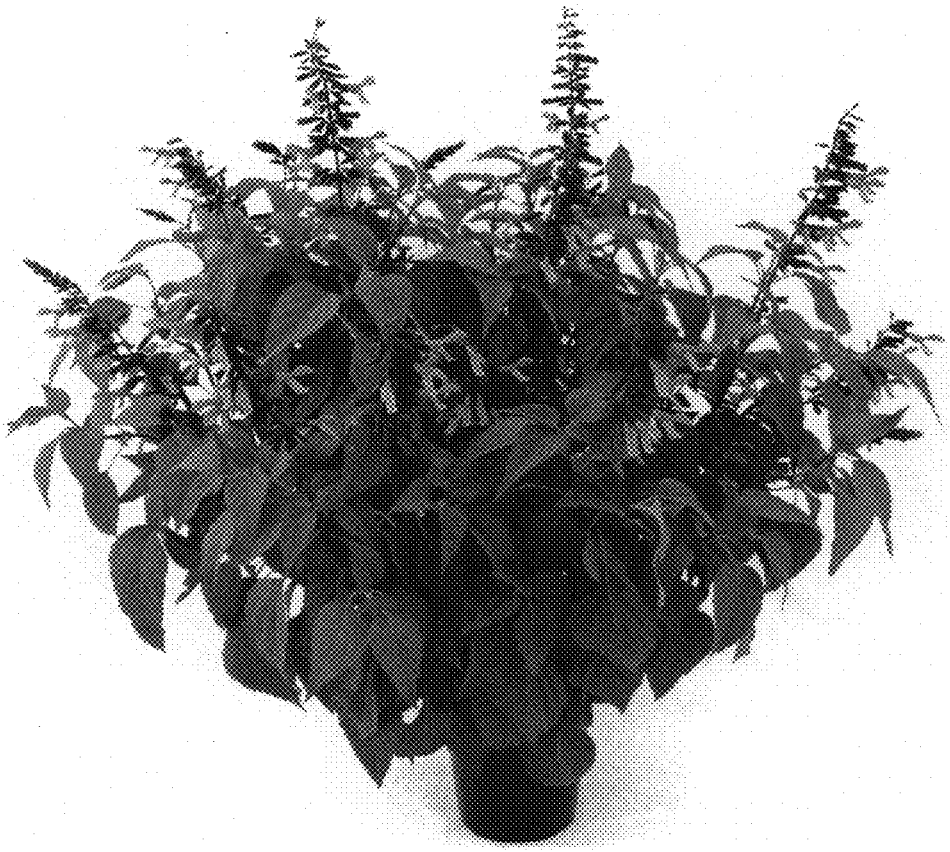
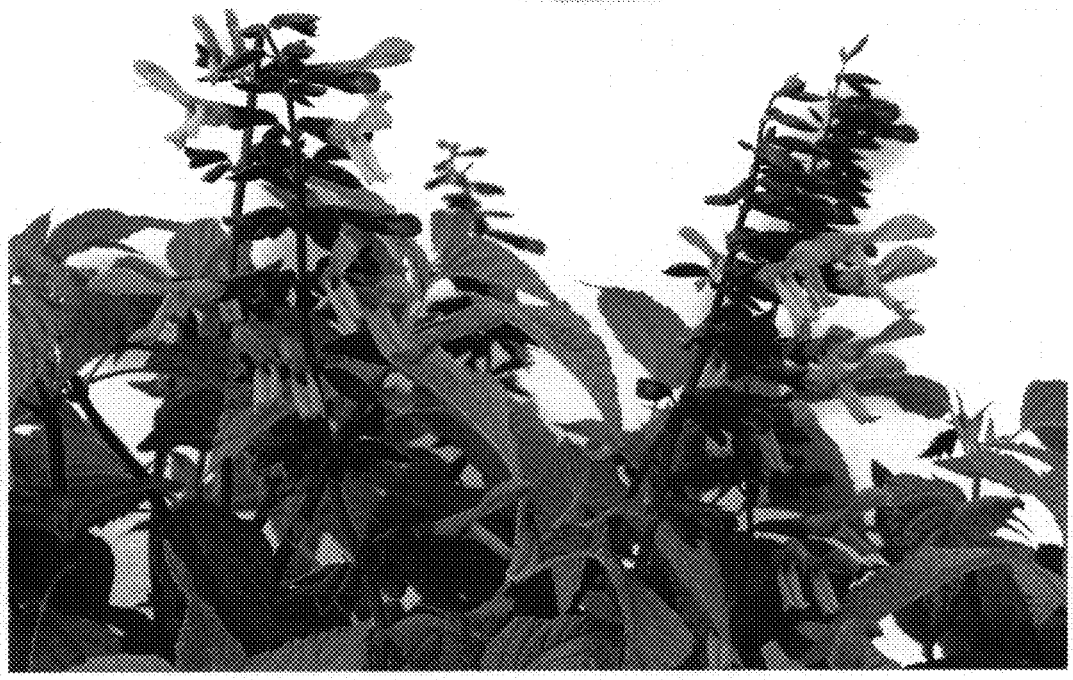

* * * * *